United States Patent [19]

Schuurs et al.

[11] 4,254,223
[45] Mar. 3, 1981

[54] APPARATUS FOR COLORIMETRIC DETERMINATION

[75] Inventors: Antonius H. W. M. Schuurs, Oss; Johannes H. W. Leuvering, Heesch, both of Netherlands

[73] Assignee: Akzona Incorporated, Asheville, N.C.

[21] Appl. No.: 30,515

[22] Filed: Apr. 16, 1979

[30] Foreign Application Priority Data

Apr. 18, 1978 [NL] Netherlands ......................... 7804144

[51] Int. Cl.³ ............................................. C12M 1/24
[52] U.S. Cl. ................................... 435/296; 356/246; 356/440; 422/73; 435/7; 435/291; 435/808
[58] Field of Search ................. 356/246, 440; 422/73, 422/102; 435/4, 7, 291, 808, 287, 296

[56] References Cited

U.S. PATENT DOCUMENTS

| 2,580,500 | 1/1952 | McHalbert | 356/442 |
|---|---|---|---|
| 3,141,094 | 7/1964 | Strickler | 250/574 |
| 3,263,553 | 8/1966 | Baruch | 250/574 |
| 3,448,277 | 6/1979 | Jayko | 250/573 |
| 3,627,432 | 12/1971 | Bermann | 422/102 |
| 3,654,090 | 4/1972 | Schuurs et al. | 435/188 |
| 3,692,410 | 9/1972 | Jurany et al. | 356/40 |
| 3,740,155 | 6/1973 | Keller et al. | 356/246 |
| 3,791,932 | 2/1974 | Schuurs et al. | 435/7 |
| 3,932,763 | 1/1976 | Weinstein | 356/246 |
| 4,016,043 | 4/1977 | Schuurs et al. | 435/7 |
| 4,075,062 | 2/1978 | Shibata et al. | 435/808 |

FOREIGN PATENT DOCUMENTS

| 2040481 | 2/1972 | Fed. Rep. of Germany | 356/246 |
|---|---|---|---|
| 1533412 | 7/1968 | France . | |
| 1536119 | 8/1968 | France . | |
| 856617 | 12/1960 | United Kingdom . | |

Primary Examiner—Peter A. Hruskoci
Attorney, Agent, or Firm—Robert H. Falk; Charles A. Wendel; Francis W. Young

[57] ABSTRACT

An apparatus for use in the colorimetric determination of liquids is disclosed wherein the apparatus is a reaction vessel having a massive V-shaped bottom of transparent material with a refractive index of $n \geq 1.4$. The bottom has a cone- or prism-shape with an apical angle from about 80° to about 100° or the shape of a polyhedral pyramid whose opposing surfaces intersect at an angle between about 80° and about 100°. The apparatus permits speeded-up colorimetric determinations.

8 Claims, 3 Drawing Figures

APPARATUS FOR COLORIMETRIC DETERMINATION

BACKGROUND OF THE INVENTION

1. Field of the Invention

The invention relates to an apparatus for performing colorimetric determinations of liquids.

Colorimetry is a much-used technique in analytical chemistry and involves measuring the concentration of a colored component in a liquid by passing light of a certain wave-length, preferably attuned to the maximum extinction (light absorption) of the component to be determined, through the liquid under study and comparing the intensity of the transmitted light with the intensity of light transmitted by a blank. The absorption thus determined is a measure of the concentration of the component in the liquid under study.

2. Description of the Prior Art

In conventional colorimeters, samples of the liquid having a colored component whose concentration is to be determined have to be placed in cuvettes specially intended for such a purpose. This represents a substantial disadvantage in those determinations which must be performed frequently, partly because it prevents or hampers the automatization of such methods. Consequently, apparatus have become available for the determination of colorimetric reactions directly in the test tubes in which reactions have optionally been performed giving rise to situations in which it is desirable to perform a colorimetric determination in the test liquid itself to obtain further information about the nature and the course of the reaction concerned.

A known apparatus designed for this purpose, consists of a source of white light, a flexible light-guide formed of a bundle of thin glass filaments, an optical filter, a photoelectric cell with an amplifier, and a digital monitor. The flexible light-guide is divided into two compartments, one for transport of light from the light-source to the test liquid, the other for transport of the light transmitted by the liquid to be measured to the photo-electric cell, after the light has passed through the optical filter. A portion of the white light passed along the light-guide is reflected by a mirror which is placed at a set distance from the end of the light-guide. When measuring the light-absorption of the liquid under investigation, the end of the light-guide and the mirror are immersed in the liquid under investigation. Therefore, the space between the end of the light-guide and the mirror is filled with the liquid under investigation while the length of the light-path in the liquid remains constant due to the fixed distance between the mirror and the end of the light-guide. The reflected light is led to an optical filter by the second compartment of the light-guide, such that the measuring apparatus is preferably attuned to that wavelength at which the liquid under investigation shows a maximum light absorption. The intensity of the reflected and filtered light is then measured by the photo-electric cell. Comparison of the intensity of the reflected, filtered light from the liquid under investigation with that of a blank allows the light absorption of the liquid under investigation to be determined, and this may then be read from the digital monitor.

The disadvantage of this type of colorimetric determination apparatus is that the end of the flexible light-guide fitted with the mirror has to be repeatedly immersed in the liquid under investigation, which requires an effective washing procedure after each measurement to prevent mutual influence affecting the measurements obtained with various test liquids.

SUMMARY OF THE INVENTION

The present invention relates to an apparatus of such a construction that both reactions and colorimetric determinations may be performed therein, and wherein the need for immersion of the light-guide provided with a mirror at the end has been eliminated.

The apparatus for colorimetric determination of the present invention consists of a reaction vessel provided with a massive V-shaped bottom of transparent material having a refractive index of $n \geq 1.4$, the bottom being conical or prism-shaped with an apical angle lying between about 80° and about 100°, or alternatively shaped as a polyhedral pyramid, where the opposing faces intersect at an angle lying between about 80° and about 100°.

Due to the particular choice of transparent material with a given refractive index and the shape of the bottom, a light bundle that impinges from the transparent material on the sloping side of the V-shaped bottom at an angle of $\geq 45°$ from normal will be totally reflected. If the reaction vessel contains a liquid that must be colorimetrically determined, and a light-bundle is directed from above, then the light-bundle will be totally reflected from the wall of the bottom of the vessel to the other wall by the liquid and the massive transparent V-shaped bottom, where the light will again be totally reflected. The light-bundle is reflected thereafter by the bottom and the liquid.

If the incident light-bundle is divergent, the reflected light-bundle will also diverge, causing the practical difficulty of having to be certain that the position of the receiving light-guide and the width of the opening thereof are adjusted in order to collect all reflected light.

Preferably, therefore, a light-bundle is used which is parallel to the wall of the reaction vessel. Under such circumstances, the apical angle of the V-shaped bottom is preferably 90°, since the reflected light-bundle will be parallel also, and can readily be collected "in toto", which is beneficial for the sensitivity of the colorimetric determination (see FIG. 1).

DESCRIPTION OF THE PREFERRED EMBODIMENT

The V-shaped bottom may be composed from any transparent material, such as glass or transparent plastics, provided that the refractive index of the material is equal to or greater than 1.4. The material that borders on the outside of the V-shaped bottom is generally air, but it is also possible to have the V-shaped bottom embedded in another material, or coated with a not-too-thin layer of another material. In these cases, it is necessary that the refractive index of the transparent material ($n_1$) be $\geq 1.4$ and that the ratio of $n_1$ to the refractive index of the bordering material ($n_2$) is such that $n_2/n_1 < \frac{1}{2}\sqrt{2}$ ($=0.7$). The advantage of this last embodiment is that the critical angle is not affected if fluid or other substances with unsuitable refractive indices are deposited on the underside of the V-shaped bottom, thus allowing total reflection to continue to take place.

The V-shaped bottom of the reaction vessel may optionally also be truncated.

It is preferred that the upper side of the V-shaped bottom, i.e., the bottom of the internal reaction vessel, is at an angle of 90° to the axis of the reaction vessel. It is also possible that the upper side of the V-shaped bottom is curved, with a curvature opposite that of the surface of the liquid, so that the refraction of the light-bundle caused by the meniscus of the surface of the liquid is canceled by the upper side of the transparent material.

The form of the reaction vessel bottom does not have to correspond to the form of the reaction vessel interior. The latter may, for example, be square or rectangular, while the massive bottom may be a cone or a polyhedral pyramid, or the interior of the reaction vessel may be cylindrical while the bottom, for example, has a pyramidal structure.

Figure 1:
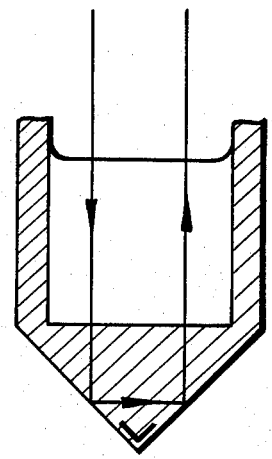
Figure 2:
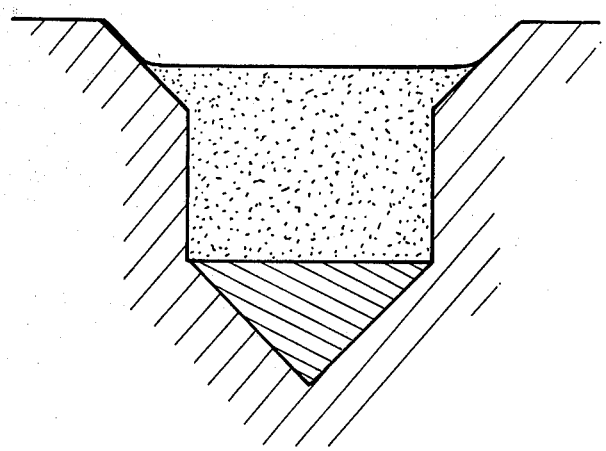

The measurements may be unfavorably affected by the curvature of the liquid surface in the reaction vessel, particularly when the diameter of the latter is small. This disadvantage can be overcome by making the upper part of the reaction vessel funnel-shaped such that the curvature of the liquid surface occurs at the sides of the funnel and the liquid surface above the reaction vessel proper is flat (see FIG. 2).

Figure 3:
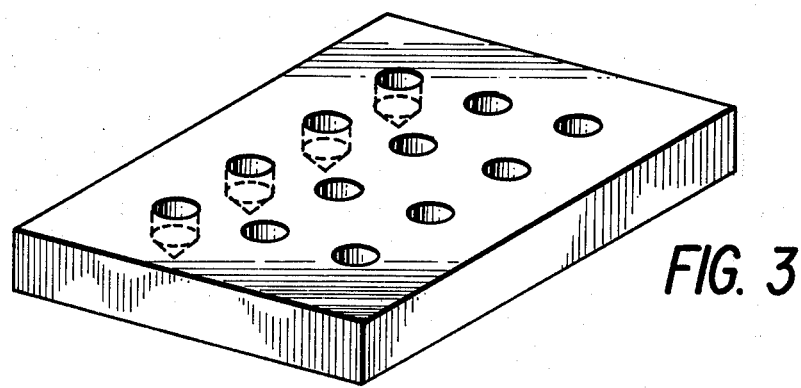

The apparatus described above may also constitute a portion of a construction that contains a number of such reaction vessels, e.g., a micro-titration plate which is particularly suitable for the automatization of determinations to be performed in large numbers of liquid samples (see FIG. 3).

The apparatus according to the present invention may be used for the colorimetric determination of liquids in general. It is particularly useful in the enzyme immuno-assay (EIA) developed about 1970, as shown in U.S. Pat. Nos. 3,654,090; 3,791,932; and 4,016,043. EIA relates to a method for the determination of immunological components such as haptens, antigens,, and antibodies, by using such a component coupled to an enzyme. The immunological reaction proper may then be performed in the apparatus according to the present invention, after which the enzyme determination may take place in the same vessel by adding both an enzyme substrate and a substance which is converted under the influence of the subsequent enzyme reaction into a colored substance or conversely, is converted into a colorless substance.

The increase or decrease in color may subsequently be colorimetrically determined in the same vessel, whereby the light absorption is a measure of the immunological component to be determined.

For the application described above, the inside of the test apparatus according to the present invention is preferably coated with an immunological component such as an antigen, antibody, hapten, or anti-antibody. The binding between such a component and the inside wall of the reaction vessel is preferably of a physical nature, but it may also be brought about by a chemical binding reaction.

The colorimetric determination may be performed with an aid of a flexible light-guide, such as noted above, which is optionally of the same shape as the reaction vessel and/or the V-shaped bottom, e.g., cylindrical, rectangular, square, or polygonal, whereby this apparatus is divided into two equal compartments. The incident light-bundle is guided through the one compartment, and the light-bundle, after being reflected twice, leaves in a direction opposite to the incident light-bundle and is guided by the other compartment of the light-guide, after which the intensity of the emergent light-bundle is measured with the aid of a photoelectric cell. The light-bundle may also consist of two separate parts, one for the introduction of light and another for the transmission of the reflected light.

What is claimed is:

1. An apparatus for use in performing colorimetric determinations of liquids comprising a reaction vessel for the liquid provided with a solid V-shaped bottom of transparent material having a refractive index of $n \geq 1.4$, said bottom having a cone- or prism-shape with an apical angle from about 80° to about 100°, or the shape of a polyhedral pyramid whose opposing surfaces intersect at an angle between about 80° and about 100°.

2. The apparatus of claim 1 wherein said V-shaped bottom has an angle of about 90°.

3. An apparatus for use in performing colorimetric determinations of liquids comprising at least one reaction vessel for the liquids provided with a solid V-shaped bottom of transparent material having a refractive index of $n \geq 1.4$, said bottom having a cone- or prism-shape with an apical angle from about 80° to about 100°, or the shape of a polyhedral pyramid whose opposing surfaces intersect at an angle between about 80° and about 100°, wherein said V-shaped bottom has an outside border of a material other than air and wherein the ratio of the refractive index of the outside border material to the refractive index of the transparent material is less than or equal to $\frac{1}{2}\sqrt{2}$.

4. The apparatus of claim 3 comprising a plurality of said reaction vessels.

5. The apparatus of claim 3 wherein the inside of said vessel is coated with an immunological component.

6. The apparatus of claim 5 wherein said immunological component is selected from the group consisting of an antigen, an antibody, a hapten, and an anti-antibody.

7. An apparatus for use in performing colorimetric determinations or liquids comprising a reaction vessel for the liquids having a cylindrical upper portion and provided with a solid V-shaped bottom of transparent material having a refractive index of $n \geq 1.4$, said bottom having a cone- or prism-shape with an apical angle from about 80° to about 100°, or the shape of a polyhedral pyramid whose opposing surfaces intersect at an angle between about 80° and about 100°, wherein said V-shaped bottom has an outside border of a material other than air and wherein the ratio of the refractive index of the outside border material to the refractive index of the transparent material is less than or equal to $\frac{1}{2}\sqrt{2}$.

8. An apparatus for use in performing colorimetric determination of liquids comprising a reaction vessel for the liquids having a cylindrical upper portion and provided with a solid V-shaped bottom of transparent material having a reflective index of $n \geq 1.4$, said bottom having a cone- or prism-shape with an apical angle from about 80° to about 100°, or the shape of a polyhedral pyramid whose opposing surfaces intersect at an angle between 80° and about 100° C., wherein said V-shaped bottom has an outside border of air.

* * * * *

UNITED STATES PATENT OFFICE
CERTIFICATE OF CORRECTION

Patent No. 4,254,223          Dated March 3, 1981

Inventor(s) A.H.W.M. SCHUURS and J.H.W. LEUVERING

It is certified that error appears in the above-identified patent and that said Letters Patent are hereby corrected as shown below:

On the title page, under "References Cited, U.S. Patents, correct the identity of the following references as follows:

| | | |
|---|---|---|
| 2,580,500 | 1/52 | McH. Albert |
| . | | |
| . | | |
| . | | |
| 3,448,277 | 6/69 | Jayko |
| . | | |
| . | | |
| 3,627,432 | 12/71 | Bergmann |
| . | | |
| . | | |
| 3,692,410 | 9/72 | Jurány et al. |

Under "Foreign Patent Documents", correct the identity of the references as follows:

| | | |
|---|---|---|
| 2,040,481 | 2/1972 | Fed. Rep. of Ger... 356/246 (Offlegungsschrift) |
| 1,533,412 | 9/1968 | |
| 1,536,119 | 6/1968 | |
| . | | |
| . | | |
| . | | |

UNITED STATES PATENT OFFICE
CERTIFICATE OF CORRECTION

Patent No. 4,254,223          Dated  March 3, 1981

Inventor(s) A.H.W.M. SCHUURS and J.H.W. LEUVERING

It is certified that error appears in the above-identified patent and that said Letters Patent are hereby corrected as shown below:

In Col. 1, line 6, underline "Field of the Invention".

In Col. 1, line 19, underline "Description of the Prior Art".

Signed and Sealed this

First Day of September 1981

[SEAL]

Attest:

Attesting Officer

GERALD J. MOSSINGHOFF

Commissioner of Patents and Trademarks